(12) United States Patent
Roth

(10) Patent No.: US 6,569,649 B2
(45) Date of Patent: *May 27, 2003

(54) COMPOSITIONS AND METHODS FOR SACCHARIDE SYNTHESIS

(75) Inventor: Stephen Roth, Gladwyne, PA (US)

(73) Assignee: The Trustees of the University of Pennsylvania, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/484,885

(22) Filed: Jun. 7, 1995

(65) Prior Publication Data

US 2002/0045222 A1 Apr. 18, 2002

Related U.S. Application Data

(63) Continuation of application No. 08/275,664, filed on Jul. 15, 1994, now abandoned, which is a continuation of application No. 07/853,872, filed on Mar. 17, 1992, now abandoned, which is a continuation of application No. 07/509,560, filed on Apr. 16, 1990, now abandoned.

(51) Int. Cl.$^7$ ............................ C12P 19/18; C12P 19/12

(52) U.S. Cl. ........................ 435/97; 435/84; 435/68.1; 435/193; 435/814; 435/815

(58) Field of Search ............................... 435/193, 815, 435/68.1, 97, 84, 814

(56) References Cited

U.S. PATENT DOCUMENTS

| | | | |
|---|---|---|---|
| 4,150,116 A | 4/1979 | Taubman et al. ............ 424/88 |
| 4,184,917 A | 1/1980 | Dorner et al. .............. 435/68 |
| 4,219,571 A | 8/1980 | Miyake .................... 426/48 |
| 4,261,976 A | 4/1981 | Isselbacher et al. ........ 530/322 |
| 4,359,531 A | 11/1982 | Bucke et al. ............. 426/536 |
| 4,386,158 A | 5/1983 | Shimizu et al. ............ 435/97 |
| 4,537,763 A | 8/1985 | Miyake et al. |
| 4,557,927 A | 12/1985 | Miyake et al. |
| 4,563,445 A | 1/1986 | Feizi et al. ............... 514/25 |
| 4,569,909 A | 2/1986 | Seno et al. ............... 435/89 |
| 4,590,160 A | 5/1986 | Nishihashi et al. ......... 435/78 |
| 4,594,321 A | 6/1986 | Fujishima et al. .......... 435/89 |
| 4,617,269 A | 10/1986 | Rathbone et al. ........... 435/97 |
| 4,621,137 A | 11/1986 | Miyake et al. ............. 536/5 |
| 4,624,919 A | 11/1986 | Kokusho et al. ............ 435/74 |
| 4,670,387 A | 6/1987 | Bucke et al. .............. 435/97 |
| 4,678,747 A | 7/1987 | Lloyd et al. .............. 435/7 |
| 4,683,198 A | 7/1987 | Ishikawa et al. ........... 426/97 |
| 4,683,297 A | 7/1987 | Yanami et al. ............. 536/18.6 |
| 4,693,974 A | 9/1987 | Schwengers et al. ......... 435/97 |
| 4,757,012 A | 7/1988 | Estell et al. ............. 435/172.3 |
| 4,770,994 A * | 9/1988 | Rittenhouse .............. 435/963 |
| 4,782,019 A | 11/1988 | Kokusho et al. ............ 435/89 |
| 4,818,816 A | 4/1989 | Petitou et al. ............ 536/55.2 |
| 4,835,105 A | 5/1989 | Seres et al. .............. 435/97 |
| 4,835,264 A | 5/1989 | Liav et al. ............... 536/4.1 |
| 4,849,356 A | 7/1989 | Van Dooren et al. ........ 435/183 |
| 4,851,517 A | 7/1989 | Feder et al. .............. 536/1.1 |
| 4,855,128 A | 8/1989 | Lynch et al. .............. 424/49 |
| 4,859,590 A | 8/1989 | Thiem et al. .............. 435/97 |
| 4,865,976 A | 9/1989 | Rohrbach et al. ........... 435/103 |
| 4,868,104 A | 9/1989 | Kurn et al. ............... 435/6 |
| 4,876,195 A | 10/1989 | Shirafuji et al. .......... 435/137 |
| 4,900,822 A | 2/1990 | von der Eltz et al. ....... 544/102 |
| 4,912,093 A | 3/1990 | Michaeli .................. 514/33 |
| 4,918,009 A | 4/1990 | Nilsson .................. 435/73 |
| 4,925,796 A | 5/1990 | Bergh et al. .............. 435/97 |
| 4,931,389 A | 6/1990 | Kobayashi et al. .......... 435/95 |
| 4,943,630 A | 7/1990 | Jacquinet et al. .......... 536/123 |
| 5,032,519 A * | 7/1991 | Paulson et al. ............ 435/193 |
| 5,246,840 A | 9/1993 | Nilsson .................. 435/101 |
| 5,874,261 A * | 2/1999 | Roth ..................... 435/97 |

FOREIGN PATENT DOCUMENTS

| | | |
|---|---|---|
| EP | 84850211.8 | 2/1985 |
| EP | 356048 * | 2/1990 |
| WO | WO A 89/09275 | 10/1989 |
| WO | WO 90/05304 | 5/1990 |

OTHER PUBLICATIONS

Urban et al, Biochem. Soc. Trans. 6:172–174 1978.*
*Affinity Chromatography, Principles and Methods*, Pharmaca Biotechnology, Sweden, 1988.*
Carlson et al, J. Biol. Chem. 248(16):5763–5773, 1973.*
Weinstein, J. et al., "Purification of a GalB1–4Glc NAcα2–6 Sialytransferase . . . Rat Liver", *J of Biol Chem*, vol. 257, No. 22, pp. 13835–13844, 1982.*
Parodi et al., Biomedicine, 28, pp. 9–13, 1978.*
*The Merck Index*, Tenth Edition, Index No. 8320, 1983.*
Toone et al., Tetrahedron, vol. 45, No. 17, pp. 5365–5422 (1989).
Nilsson, Immunochemistry, vol. 110, Abstract 110:6111y, p. 581 (1989).
Thiem et al, Angew. Chem. Int. Ed. Engl. 25, No. 12, pp. 1096–1097 (1986).
Nunez et al., Biochemistry, vol. 19, No. 3, pp. 489–495 (1980).
Zehavi et al., Carbohydrate Research, *133*, pp. 339–342 (1984).

(List continued on next page.)

*Primary Examiner*—Francisco Prats
(74) *Attorney, Agent, or Firm*—Morgan, Lewis & Bockius, LLP

(57) ABSTRACT

Processes for preparing oligosaccharides, polysaccharides, glycolipids, glycoproteins, and other saccharide compositions are provided which involve the enzyme facilitated transfer of a preselected saccharide unit from a donor moiety to an acceptor moiety. In accordance with a preferred embodiment, saccharide compositions having a plurality of saccharide units are prepared by appending the saccharide units in iterative fashion to acceptor moieties which are themselves saccharide compositions prepared in accordance with this invention.

9 Claims, No Drawings

OTHER PUBLICATIONS

Zehavi et al., Carbohydrate Research, 128, pp. 160–164 (1984).
Sadler et al., Methods in Enzymology, vol. 83, pp. 458–493 (1982).
Cote et al., Chemical Abstracts, vol. 113, Abstract no. 113:187372q (1990).
Kitahata, Chemical Abstracts, vol. 111, Abst. No. 111:93061u, p. 355 (1989).
Kitahata, Chemical Abstracts, vol. 113, Abst. No. 113:170336h, p. 567 (1990).
Katsumi et al., Chemical Abstracts, vol. 111, Abst. No. 111:152000y, p. 565 (1989).
Auge et al., Carbohydrate Research, 151, pp. 147–156 (1986).
Auge et al., Carbohydrate Research, 200, pp. 257–268 (1990).
Auge et al., Carbohydrate Research, 193, pp. 288–293 (1989).
Sabesan et al., J. Am. Chem. Soc., vol. 108, No. 8, pp. 2068–2080 (1986).
Closs et al., J. Org. Chem., vol. 47, No. 27, pp. 5416–5418 (1982).
Creeger et al., J. Biol. Chem., vol. 254, No. 3, pp. 804–810 (1979).
Demers et al., J. of Applied Biochemistry, vol. 7, pp. 122–125 (1985).
Furukawa et al., Biochem. J., vol. 227, pp. 573–582 (1985).
Roth et al., Experimental Cell Research, vol. 143, pp. 217–225 (1983).
Benau et al., J. of Histochemistry and Cytochemical, vol. 38, No. 1, pp. 23–30 (1990).
Thomas Schaal et al., Glycoconjugate Journal, vol. 7, No. 5, p. 475 (1990).
Wong, C.H., 1989, Science 244, 1145–1152.
Suganuma, T., et al., *J. Biochem.*, 1987, 102, 665–671.
Rosevear, P.R., et al., *Biochemistry*, 1982, 21 1421–1431.
Pollak, A., et al., *J. Am. Chem. Soc.*, 1980, 102, 6324–36.
Barker, R., *J. Biol. Chem.*, 1972, 247, 7135–7147.
Elices, M.J. and Goldstein, I.J., *Archives of Biochemistry and Biophysics*, 1987, 254, 239–341.
Palcic, M.M., *Carbohydrate Research*, 1989, 190, 1–11.
Palcic, M.M., *Carbohydrate Research*, 1987, 159, 315–324.
Sheares, B.T. and Carlson, D.M., *J. Biol. Chem.*, 1983, 258, 9893–9898.
Cartron, J.P., et al., *FEBS Letters*, 1976, 67, 143–148.
Zehavi, U., et al., *Carbohydrate Research*, 1983, 124, 23–24.
Appert, H.E., et al., *Biochemical and Biophysical Research Communications*, 1986, 139, 163–168.
Narimatsu, H., et al., *Proc. Natl. Acad. Sci. USA*, 1986, 83, 4720–4724.
van den Eijnden, D.H. et al., *J. Biol. Chem.* 1988, 263, 12461–12471.
Zubay, *Biochemistry*, 2nd Edition, Macmillan Publishing Company, 709–712 (1988).
Palcic et al., *Glycobiology* 1(2):205–209 (1991).
Yoon et al., *Glycobiology* 2(2):161–168 (1992).
Amado et al., *Biochimica et Biophysica Acta* 1473, 35–53 (1999).

Brew et al., 1968, "The Role of α–Lactalbumin and the A Protein in Lactose Synthetase: A Unique Mechanism for the Control of a Biological Reaction," *Biochemistry* 59:491–497.
Trayer et al., 1971, "The Purification and Properties of the A Protein of Lactose Synthetase," *J. Biol. Chem.* 246(21):6666–6675.
Hagopian et al., 1968, "Glycoprotein Biosynthesis: Studies on the Receptor Specificity of the Polypeptidyl: N–Acetylgalactosaminyl Transferase from Bovine Submaxillary Glands," *Arch. Biochem. and Biophys.* 128:422–433.
Sadler et al., 1979, "Purification to Homogeneity of a β–Galactoside a2→3 Sialytransferase and Partial Purification of an α–N–Acetylgalactosaminide a2→6 Sialytransferase from Porcine Submaxillary Glands," *J. Biol. Chem.* 254(11):4434–4443.
Sadler et al., 1979, Purification to Homogeneity and Enzymatic Characterization of an αN–Acetylgalactosaminide a2→6 Sialytransferase from Porcine Submaxillary Glands, *J. Biol. Chem.* 254(13):5934–5941.
Sadler et al., 1982, "Purification of Mammalian Glycosyltransferases," *Methods in Enzymology* 83:458–514.
Beyer, et al., 1981, *Advances in Enzymology* 52:24–175.
Carbohydrate Research, vol. 137, pp. 39–62, Mar. 29, 1985, H. Paulsen, et al., "Synthese der Tetraund Trisaccharid–Sequenzen von Asialo–Gm1 Und–Gm2 Lenkung der Regioselektivitat der Glycosidierung von Lactose".
The Journal of Biological Chemistry, vol. 265, No. 9, pp. 4859–4862, Mar. 25, 1990, H.Kitagawa, et al., "Occurrance of Tetra–and Pentasaccharides with the Sialyl–LEa Structure in Human Milk".
Chemical Abstracts, vol. 74, No. 7, p. 167, No. 29979q, Feb. 15, 1971, H. Takizawa, et al., "Blood Group Substances from Human Erythrocytes. II. Structural Analysis by Methylation of Blood Group–Active Oligosaccharides".
Biochemistry, vol. 21, No. 6, pp. 1421–1431, Mar. 16, 1982, P.R. Rosevear, et al., "Synthesis and Solution Conformation of the Type 2 Blood Group Oligosaccharide AlphaFuC(1–2) BETADGa (1–4)BETADG1cNac".
Chemical Abstracts, vol. 94, No. 15, issued Apr. 13, 1981 Iman et al., "Isolation and Characterization of a major glycoprotein from milk–fat–globule membrane of human breast milk", see p. 229, columns 1 and 2, Abstract No. 116282p, Biochemistry Journal, 193(1), 47–54.
Chemical Abstracts, vol. 91, No. 13, issued Sep. 24, 1979, Chatterjee, et al., "Glycosyltransferase and glycosidase activities in ovarian cancer," see p. 446, col. 1, Abstract No. 1063005, Cancer Res., 36(6,PT.1), 1943–51.
Chemical Abstracts, vol. 114, No. 9, issued Mar. 4, 1991, De Stafano et al., "Analysis of *Pneumocystis carinii* cyst wall. II Sugar Composition," see pp. 389 and 390, columns 2 and 1 abstract No. 78313w, J. Protozool., 37(5), 436–41.
Chemical Abstracts, vol. 109, No. 17, issued Oct. 24, 1988, Krivan et al., "Many pulmonary pathogenic bacteria bind specifically to the carbohydrate sequence GalNAc β1–4 Gal found in some glycolipids," see p. 421, col. 2, Abstract No. 146217S, Proc.Natl. Acad. Sci. U.S.A. 85(16), pp. 6157–6.

* cited by examiner

COMPOSITIONS AND METHODS FOR SACCHARIDE SYNTHESIS

This application is a Continuation of application Ser. No. 08/275,664, filed on Jul. 15, 1994, now abandoned, which is a Continuation application of Ser. No. 07/853,872, filed on Mar. 17, 1992, abandoned, which is a Continuation application of Ser. No. 07/509,560, filed on Apr. 16, 1990, abandoned.

RELATED APPLICATION

This application relates to subject matter disclosed in copending U.S. patent application Ser. No. 241,012, filed Sep. 2, 1988, entitled "Carbohydrates and Carbohydrate Complexes for Therapeutic and Preventative Treatment of Mammals". Ser. No. 241,012 is incorporated herein by reference.

GOVERNMENT SUPPORT

Portions of this invention were supported by National Science Foundation Grant DCB8817883.

FIELD OF THE INVENTION

This invention relates to saccharide compositions such as, for example, oligosaccharides, polysaccharides, glycolipids, and glycoproteins. More specifically, this invention relates to processes for preparing these and other saccharide compositions by enzymatic techniques.

BACKGROUND OF THE INVENTION

The term "carbohydrate" embraces a wide variety of chemical compounds having the general formula $(CH_2O)_n$, such as monosaccharides, disaccharides, oligosaccharides and polysaccharides. Oligosaccharides are chains composed of saccharide units, which are alternatively known as sugars. These saccharide units can be arranged in any order and the linkage between two saccharide units can occur in any of approximately ten different ways. As a result, the number of different possible stereoisomeric oligosaccharide chains is enormous.

Of all the biological polymer families, oligosaccharides and polysaccharides have been the least well studied, due in considerable part to the difficulty of sequencing and synthesizing their often complex sugar chains. Although the syntheses of oligonucleotides and polypeptides are well developed, there is currently no generally applicable synthetic technique for synthesizing oligosaccharides. Organic synthesis of oligosaccharides is further hampered by the lability of many glycosidic bonds, difficulties in achieving regioselective sugar coupling, and generally low synthetic yields.

Much research effort has been devoted to carbohydrates and molecules comprising carbohydrate fragments, such as glycolipids and glycoproteins. Research interest in such moieties has been largely due to the recognition that interactions between proteins and carbohydrates are involved in a wide array of biological recognition events, including fertilization, molecular targeting, intercellular recognition, and viral, bacterial, and fungal pathogenesis. It is now widely appreciated that the oligosaccharide portions of glycoproteins and glycolipids mediate recognition between cells and cells, between cells and ligands, between cells and the extracellular matrix, and between cells and pathogens.

These recognition phenomena can likely be inhibited by oligosaccharides having the same sugar sequence and stereochemistry found on the active portion of a glycoprotein or glycolipid involved in cell recognition. The oligosaccharides are believed to compete with the glycoproteins and glycolipids for binding sites on receptor proteins. For example, the disaccharide galactosyl β 1-4 N-acetylglucosamine is believed to be one component of the glycoproteins which interact with receptors in the plasma membrane of liver cell. Thus, to the extent that they compete with potentially harmful moieties for cellular binding sites, oligosaccharides and other saccharide compositions have the potential to open new horizons in pharmacology, diagnosis, and therapeutics.

There has been relatively little effort to test oligosaccharides as therapeutic agents for human or animal diseases, however, as synthetic methods for oligosaccharides have been unavailable. Limited types of small oligosaccharides can be custom-synthesized by organic chemical methods, but the cost for such compounds is typically very high. In addition, it is very difficult to synthesize oligosaccharides stereospecifically and the addition of some sugars, such as sialic acid and fucose, has not been effectively accomplished because of the extreme lability of their bonds. Improved, generally applicable methods for oligosaccharide synthesis are desired for the production of large amounts of widely varying oligosaccharides for pharmacology and therapeutics.

For certain applications, enzymes have been targeted for use in organic synthesis as one alternative to more traditional techniques. For example, enzymes have been used as catalysts in organic synthesis; the value of synthetic enzymatic reactions in such areas as rate acceleration and stereoselectivity has been demonstrated. Additionally, techniques are now available for low cost production of some enzymes and for alteration of their properties. Environmental concerns and regulatory constraints faced in the chemical and pharmaceutical industries have spurred hope that enzymatic methods may offer clean and mild processes. To date, however, enzymatic techniques have not been found which are useful for the general synthesis of oligosaccharides and other complex carbohydrates in significant amounts.

Accordingly there exists a long-felt need for general synthetic methods for the production of oligosaccharides, glycoproteins, glycolipids, and similar species in an efficient, cost effective, stereospecific, and generally applicable manner.

OBJECTS OF THE INVENTION

It is an object of the present invention to provide saccharide compositions, particularly oligosaccharides and chemical moieties which comprise oligosaccharide units.

It is another object of this invention to provide a wide variety of saccharide compositions, including those not found in nature. It is a further object of this invention to provide saccharide compositions useful in mitigating the effects of human or animal diseases.

It is yet another object of this invention to provide improved processes for preparing saccharide compositions.

It is a further object of this invention to provide enzymatic processes for preparing saccharide compositions.

It is still another object of this invention to provide processes for preparing enzymes useful in synthesizing saccharide compositions.

SUMMARY OF THE INVENTION

These and other objects are achieved by the present invention, which provides enzymatic processes for preparing oligosaccharides, polysaccharides, glycolipids, glycoproteins, and other saccharide compositions. These processes involve the enzyme-facilitated transfer of a preselected saccharide unit from a donor moiety to an acceptor moiety. Saccharide compositions having a plurality of saccharide units are preferably prepared by appending the saccharide units in stepwise fashion to acceptor moieties which are themselves saccharide compositions prepared in accordance with this invention.

Accordingly, methods for preparing saccharide compositions are provided comprising the steps of providing an acceptor moiety and contacting the acceptor moiety with a glycosyltransferase. The glycosyltransferase is prepared so as to be specific for the acceptor moiety and capable of transferring a saccharide unit to the acceptor moiety. Also provided are reaction conditions and co-reagents as may be necessary and sufficient to effect the covalent bonding of the saccharide unit to the acceptor moiety.

In accordance with preferred embodiments, the acceptor moiety may be a protein, glycoprotein, lipid, glycolipid, or carbohydrate, such as a monosaccharide, disaccharide, oligosaccharide, or polysaccharide. In accordance with other preferred embodiments, the glycosyltransferase is attached to a solid support.

The present methods are capable of stereospecific attachment of the saccharide unit to the acceptor moiety. In general, it is preferred to employ saccharide nucleotides as donor moieties. Uridine, guanosine, and cytidine phosphate materials terminated by the saccharide units to be donated preferably comprise the donor moieties.

It is also preferred to perform the methods of the present invention a plurality of times such that the product of the first iteration becomes the acceptor moiety for a second iteration, and so forth.

The saccharide compositions prepared in accordance with this invention are believed to find wide utility in diagnostics, therapeutics, and pharmacological applications. The present invention also provides means for preparing a glycosyltransferase specific for a particular acceptor moiety and capable of transferring a preselected saccharide unit to the acceptor moiety. Such methods comprise contacting the acceptor moiety with a mixture suspected to contain a plurality of glycosyltransferases under conditions effective to bind the acceptor moiety and the glycosyltransferase specific for the acceptor moiety. The resulting, bound glycosyltransferase is subsequently isolated. It is preferred that the glycosyltransferase be sequenced and that the glycosyltransferase be produced in enhanced quantities for genetic engineering techniques.

DETAILED DESCRIPTION OF THE INVENTION

As employed herein, the term "saccharide composition" is intended to include any chemical moiety having a saccharide unit within its structure. Sugars, carbohydrates, saccharides, monosaccharides, oligosaccharides, polysaccharides, glycoproteins, and glycolipids provide examples of saccharide compositions. Mixtures and solutions comprising such moieties are also saccharide compositions.

Saccharide compositions are prepared according to this invention by the enzyme facilitated transfer of saccharide units from donor moieties to acceptor moieties. It will be appreciated that such transfer occurs upon contacting the acceptor and donor moieties with a glycosyltransferase, and typically results in covalently bonding of the acceptor moiety and the saccharide unit stereoselectively, that is, in but one stereoisomeric form.

Once the sugar sequence of a desired target saccharide composition has been determined by conventional methods, a retrosynthetic analysis is generally performed to determine an appropriate synthetic scheme for the saccharide composition. Such a synthetic scheme preferably identifies the particular donor moieties, acceptor moieties, and glycosyltransferases necessary to yield the desired saccharide composition.

In accordance with the present invention, an acceptor moiety is provided which is capable of being covalently bound to a preselected saccharide unit. Representative acceptor moieties include proteins, glycoproteins, lipids, glycolipids and carbohydrates. It will be appreciated that acceptor moieties are preferred to the extent that they are present as a structural component of a saccharide composition of interest. For example, in preparing a saccharide composition such as N-acetylneuraminyl α 2-3 galactosyl β 1-4 N-acetylglucosamine, preferred acceptor moieties would be N-acetylglucosamine and galactosyl β 1-4 N-acetylglucosamine. It will likewise be appreciated that where an acceptor moiety is terminated by a saccharide unit, subsequent saccharide units will typically be covalently bound to the nonreducing terminus of the terminal saccharide.

The saccharide unit to be transferred to an acceptor moiety is provided by a donor moiety for the saccharide unit. A donor moiety according to this invention includes the saccharide unit to be transferred and is capable of providing that saccharide unit to the acceptor moiety when contacted by the acceptor moiety and the appropriate glycosyltransferase. Preferred donor moieties are saccharide nucleotides, such as saccharide-terminated uridine phosphates, saccharide-terminated guanosine phosphates, and saccharide-terminated cytidine phosphates. It will be appreciated that donor moieties are preferred to be capable of readily providing their component saccharide unit to an acceptor moiety when placed in contact therewith and with a glycosyltransferase. For example, uridine diphosphate galactose is preferred for transferring galactose to N-acetylglucosamine, while cytidine monophosphate N-acetylneuraminic acid is preferred for transferring N-acetylneuraminic acid, a sialic acid, to galactosyl β 1-4 N-acetylglucosamine.

Upon identification of acceptor moieties and donor moieties necessary for the preparation of a saccharide composition, a glycosyltransferase for each acceptor/donor pair should be prepared. The present invention encompasses a method for preparing a glycosyltransferase specific for an acceptor moiety and capable of transferring a preselected saccharide unit to the acceptor moiety comprising: contacting the acceptor moiety with a mixture suspected to contain a plurality of glycosyltransferases under conditions effective to bind the acceptor moiety and glycosyltransferase specific for the specific for the acceptor moiety, wherein said contacting is in the presence of a donor moiety for the saccharide unit, providing reaction conditions and co-reagents sufficient to effect covalent bonding of the saccharide unit to the acceptor moiety, and isolating the glycosyltransferase. Those skilled in the art will appreciate that a glycosyltransferase may be broadly defined as an enzyme which facilitates the transfer of a saccharide unit from one chemical moiety (here defined as a donor) to another (here defined as an acceptor) and which is named phenomenologically according to the saccharide unit it transfers. Thus, galactosyltransferase transfers galactose, while fucosyltransferase transfers fucose.

Glycosyltransferases according to this invention are those able to effect the transfer of a predetermined saccharide unit to an acceptor moiety. Glycosyltransferases are preferably specific for an acceptor moiety or at least some significant, active, or exposed portion thereof. Specificity is manifested for a glycosyltransferase by its tendency to bind with a particularly sequenced portion of an acceptor moiety when placed in contact or close proximity therewith and to effect the transfer of a particular saccharide unit to that acceptor moiety.

Currently, glycosyltransferases are available only from natural sources and, as a result, are somewhat limited in number. It will be appreciated that known glycosyltransferases are only capable of effecting saccharide unit transfers which are highly specific, both in terms of the chemical identity of the saccharide unit transferred and the stereochemistry of its subsequent attachment to the acceptor moiety. For example, it is known that one N-acetylneuraminyltransferase can effect the transfer of N-acetylneuraminic acid to an acceptor moiety bearing only a galactose unit to produce a saccharide composition having an α 2-3 linkage between the N-acetylneuraminic acid unit and the galactose unit.

Thus, only those sugar linkages found in nature and attributable to naturally-occurring glycosyltransferases may be effected in accordance with the present invention. For example, the linkage of galactose α 1-2 to N-acetylneuraminic acid, which is not found in nature, cannot presently be effected. The methods disclosed herein are, however, applicable to any type of glycosyltransferase which may become available.

While the behavior of a number of glycosyltransferases is known, many glycosyltransferases are currently not fully characterized. The present invention, however, provides methods by which glycosyltransferases amenable to its practice may be identified and prepared. It has now been found that an acceptor moiety can be used as an affinity chromatographic tool to isolate enzymes that can be used to transfer particular saccharide units and, thus, synthesize other glycosides.

In a preferred embodiment, an acceptor moiety is immobilized as, for example, on a solid support. It will be appreciated that the term "solid support" includes semi-solid supports as well. Once immobilized, the acceptor moiety is contacted with a mixture suspected to contain glycosyltransferases, such as one comprising naturally-occurring cell homogenate. Since an immobilized acceptor moiety will bind an enzyme specific for it, this system is then carefully monitored for acceptor-bound enzyme. If no such binding occurs, then it can be concluded that the mixture did not contain an enzyme specific for the particular acceptor. Other mixtures of, for example, animal and/or plant cell homogenates are then contacted with the acceptor moiety until enzyme binding is observed.

When the acceptor moiety is bound by an enzyme, the species are separated and further studied. In a preferred embodiment, the acceptor and the candidate enzyme are again contacted, this time in the presence of a donor moiety which comprises the saccharide unit desired to be transferred to the exceptor moiety. If such contacting results in the transfer of the saccharide unit to the acceptor, the enzyme is a glycosyltransferase useful in the practice of this invention. It will be appreciated that once the glycosyltransferase is identified, it can be sequenced and/or replicated by techniques well-known to those skilled in the art. For example, replication might be accomplished by monoclonal techniques involving the isolation of genetic material coding for the glycosyltransferase and the preparation of an immortal cell line capable of producing the glycosyltransferase. Replication will likely prove desirable for commercial scale production of saccharide compositions in accordance with this invention.

After the glycosyltransferase is identified, it is contacted with the acceptor moiety and donor moiety under conditions sufficient to effect transfer and covalently bonding of the saccharide unit to the acceptor moiety. It will be appreciated that the conditions of, for example, time, temperature, and pH appropriate and optimal for a particular saccharide unit transfer can be determined by one of skill in the art through routine experimentation. Certain co-reagents may also prove useful in effecting such transfer. For example, it is preferred that the acceptor and donor moieties be contacted with the glycosyltransferase in the presence of divalent cations, especially manganese cations such as may be provided by $MnCl_2$.

In a preferred embodiment, the glycosyltransferase is immobilized by attachment to a solid support and the acceptor and donor moieties to be contacted therewith are added thereto. Alternatively, the glycosyltransferase, donor and acceptor are each provided in solution and contacted as solutes. A preferred procedure for immobilization of glycosyltransferases—and of acceptor moieties, where necessary—is based on the copolymerization in a neutral buffer of a water soluble prepolymer such as poly (acrylamide-co-N-acryloxysuccinimide (PAN), a cross-linking diamine such as triethylenetetramine, and the glycosyltransferase, as disclosed by Pollack, A., et al., *J. Am. Chem. Soc.,* 1980, 102, 6324–36. The immobilization of the enzymes on PAN is useful because small amounts of enzyme can be used, high yields of enzyme activity are obtained, and the bond between enzyme and polymer is stable. It will be appreciated that attachment of the active sites of the glycosyltransferase to the support should be avoided.

A saccharide composition prepared by contacting an acceptor moiety with a donor moiety and a glycosyltransferase can, in turn, serve as an acceptor moiety to which subsequent saccharide units may be transferred. The addition of saccharide units to saccharide compositions prepared by such contact is preferred for the synthesis of carbohydrates and saccharide chains having greater than about three saccharide units. For example, in preparing the trisaccharide N-acetylneuraminyl α 2-3 galactosyl β 1-4 N-acetylglucosamine, the disaccharide galactosyl β 1-4 N-acetylglucosamine is prepared according to this invention and then employed as an acceptor moiety to which a subsequent unit is added. Those skilled in the art will appreciate that the saccharide units attached to the saccharide compositions of this invention can be the same or different.

The saccharide compositions of this invention find use in an exceedingly wide variety of applications and may be used in the same manner as saccharide compositions available from known sources. It is preferred that the saccharide compositions be employed in therapeutic and preventative treatments for mammals, such as disclosed in U.S. Ser. No. 241,012.

The saccharide compositions of this invention are expected to find use as blocking agents for cell surface receptors in the treatment of numerous diseases of viral, bacterial, or fungal origins, such as asthma, pneumonia, rheumatoid arthritis, and diarrhea. For example, oligosaccharides prepared according to this invention may inhibit the attachment of pathogens such as pneumonia-causing bacteria to mammalian membrane molecules. Such pathogens might be incubated with cellular glycoproteins and glycolipids that have been separated by chromatography or electrophoresis. After detecting specific adherence patterns, the target compound could be analyzed and inhibitory saccharide composition prepared. If either of the complimentary molecules functions through its saccharide component, then specific saccharide compositions should inhibit attachment.

Additional objects, advantages, and novel features of this invention will become apparent to those skilled in the art upon examination of the following examples thereof, which are not intended to be limiting.

EXAMPLE 1

Preparation of the Trisaccharide N-Acetylneuraminyl α 2-3 Galactosyl β 1-4 N-Acetylglucosamine To each of five test tubes was added 10 μl of pH 7.4 potassium phosphate buffer, 10 μl of 50 mM $MnCl_2$, 17,000 cpm of cytidine monophosphate-[$^{14}$C]-N-acetylneuraminic acid, 25 μl of galactosyltransferase, and 25 μl of N-acetylneuraminyltransferase. The glycosyltransferases were purified from bovine colostrum by Sephadex G-100 gel chromatography.

To test tube 1 was also added 10 μl of 40 mM uridine diphosphate galactose and 10 μl of 40 mM N-acetylglucosamine. Test tube 1 was incubated in ice for one hour.

To test tube 2 was also added 10 μl of 40 mM uridine diphosphate galactose. Test tube 2 was incubated at 37° C. for one hour.

To test tube 3 was also added 10 μl of 40 mM N-acetyllactosamine. Test tube 3 was incubated at 37° C. for one hour.

To test tubes 4 and 5 were also added 10 μl of 40 mM uridine diphosphate galactose and 10 μl of 40 mM N-acetylglucosamine. Test tubes 4 and 5 were incubated at 37° C. for one hour.

After incubation, the contents of the test tubes were each subjected to high voltage electrophoresis on paper saturated with sodium tetraborate. Isotopically labeled trisaccharide product was identified by its mobility, as demonstrated by the product formed in test tube 3.

| Test Tube | Trisaccharide (cpm) |
|---|---|
| 1 | 0 |
| 2 | 0 |
| 3 | 3375 |
| 4 | 670 |
| 5 | 954 |

As can be seen, the presence of suitable acceptor moieties, donor moieties, and glycosyltransferases in test tubes 4 and 5 yielded the expected trisaccharide product from monosaccharide starting materials. Typically, the sialic acid N-acetylneuraminate presents special problems for synthetic organic chemists seeking to incorporate it into saccharide compositions, due to the acid lability of its glycosidic bond. Synthesizing a trisaccharide from cytidine monophosphate N-acetylneuraminic acid enzymatically eliminates the synthetic problems associated with removing protecting groups under strong acidic condition.

It is believed that an acceptor moiety (N-acetylglucosamine) initially contacts a donor moiety (uridine diphosphate galactose) and a glycosyltransferase (galactosyltransferase) to produce a saccharide composition (galactosyl β 1-4 N-acetylglucosamine), which then acts as an acceptor moiety upon contacting a second donor moiety (cytidine monophosphate N-acetylneuraminic acid) and a second glycosyltransferase (N-acetylneuraminyltransferase).

The synthesis of the trisaccharide product in test tubes 4 and 5 from monosaccharide starting materials is confirmed by comparison with the product of test tube 3, in which the trisaccharide is formed by contacting a disaccharide acceptor moiety (N-acetyllactosamine) with cytidine monophosphate N-acetylneuraminic acid and N-acetylneuraminyltransferase.

The absence of trisaccharide in test tube 2 illustrates that a suitable acceptor moiety is necessary for trisaccharide formation. The absence of trisaccharide in test tube 1 indicates that the synthesis of the trisaccharide is, indeed, dependent upon the action of any enzyme (the glycosyltransferase) that is inactive at low temperatures.

It is expected that the oligosaccharides N-acetylgalactosaminyl α 1-3 (fucosyl α 1-2) galactosyl β 1-4 N-acetylglucosaminyl β 1-3 galactose (a target for diarrhea-causing bacteria) and N-acetylgalactosaminyl β 1-4 galactosyl β 1-4 glucose (a target for pneumonia-causing bacteria) can likewise be prepared by the processes of the present invention.

What is claimed is:

1. A method for synthesizing a saccharide composition comprising preselected saccharide units, comprising:

(a) contacting an acceptor moiety with a preselected glycosyltransferase to form a acceptor moiety-glycosyltransferase intermediate;

(b) contacting the acceptor moiety-glycosyltransferase intermediate with the preselected saccharide donor moiety under conditions suitable to effect glycosyltransferase-catalyzed transfer of a preselected saccharide unit from the preselected saccharide donor moiety to the acceptor moiety to form a product;

(c) repeating steps (a) and (b) at least once such that each time said steps are repeated, the product obtained in step (b) functions as the acceptor moiety in step (a), and such that after the last time said steps are repeated, the product obtained in step (b) is the saccharide composition;

wherein each preselected glycosyltransferase contacted in step (a) is provided by a method comprising:

(i) contacting an immobilized acceptor moiety with a mixture of glycosyltransferases under conditions suitable to effect bonding of any glycosyltransferase specific for the immobilized acceptor moiety, to form a plurality of immobilized acceptor moiety-glycosyltransferase complexes;

(ii) eluting a glycosyltransferase from the plurality by contacting the plurality with the donor moiety comprising the preselected saccharide unit under conditions suitable to effect glycosyltransferase-catalyzed transfer of the preselected saccharide unit from the donor moiety to the immobilized acceptor moiety and to release the glycosyltransferase and form an immobilized product; and (iii) collecting the released glycosyltransferase.

2. A method for synthesizing a saccharide composition comprising preselected saccharide units, comprising:

(a) contacting an acceptor moiety with a preselected glycosyltransferase to form an acceptor moiety-glycosyltransferase intermediate;

(b) contacting the acceptor moiety-glycosyltransferase intermediate with a preselected saccharide donor moiety under conditions suitable to effect glycosyltransferase-catalyzed transfer of a preselected saccharide unit from the preselected saccharide donor moiety to the acceptor moiety to form a product; and (c) repeating steps (a) and (b) at least once such that each time said steps are repeated, the product obtained in step (b) functions as the acceptor moiety in step (a), and such that after the last time said steps are repeated, the product obtained in step (b) is the saccharide composition;

wherein each preselected glycosyltransferase contacted in step (a) is provided by a method comprising:

(i) contacting an acceptor moiety with a mixture of glycosyltransferases under conditions suitable to effect bonding of any glycosyltransferase specific for the acceptor moiety, to form a plurality of acceptor moiety-glycosyltransferase complexes;

(ii) eluting a glycosyltransferase from the plurality by contacting the plurality with the donor moiety comprising the preselected saccharide unit under conditions suitable to effect glycosyltransferase-catalyzed transfer of the preselected saccharide unit from the donor moiety to the acceptor moiety and to release the glycosyltransferase and form a product; and (iii) collecting the released glycosyltransferase.

3. The method of claim 1 further comprising sequencing at least one of the released glycosyltransferases, followed by replication of said released glycosyltransferase.

4. The method of claim 3 wherein said replication is accomplished by isolating genetic material coding for said released glycosyltransferase and preparation of an immortal cell line capable of producing said released glycosyltransferase.

5. The method of claim 1 or 2 wherein the acceptor moiety is a protein, a glycoprotein, a lipid, a glycolipid, or a carbohydrate.

6. The method of claim 1 or 2 wherein the saccharide donor moiety is a saccharide nucleotide.

7. The method of claim 6 wherein the saccharide nucleotide is a saccharide-terminated uridine phosphate, guanosine phosphate or cytidine phosphate.

8. The method of claim 5 wherein the carbohydrate is a monosaccharide, an oligosaccharide or a polysaccharide.

9. The method of claim 1 or 2 in which the acceptor moiety, saccharide donor moiety and the glycosyltransferases are contacted with each other in the presence of co-reagents.

* * * * *